United States Patent [19]

Schäfer et al.

[11] Patent Number: 5,747,422
[45] Date of Patent: May 5, 1998

[54] SUBSTITUTED 2-PHENYLPIRIDINES

[75] Inventors: Peter Schäfer, Ottersheim; Gerhard Hamprecht, Weinheim; Elisabeth Heistracher, Ludwigshafen; Ralf Klintz, Gruenstadt; Hartmann König, Heidelberg; Helmut Walter, Obrigheim; Karl-Otto Westphalen, Speyer; Ulf Misslitz, Neustadt, all of Germany

[73] Assignee: BASF Aktiengesellschaft, Ludwigshafen, Germany

[21] Appl. No.: 860,031

[22] PCT Filed: Jan. 4, 1996

[86] PCT No.: PCT/EP96/00008

§ 371 Date: Jul. 3, 1997

§ 102(e) Date: Jul. 3, 1997

[87] PCT Pub. No.: WO96/21646

PCT Pub. Date: Jul. 18, 1996

[30] Foreign Application Priority Data

Jan. 13, 1995 [DE] Germany .......... 195 00 911.8

[51] Int. Cl.⁶ .......... A01N 43/40; C07D 213/89
[52] U.S. Cl. .......... 504/244; 504/254; 504/255; 504/260; 504/251; 546/284.4; 546/286; 546/291; 546/304; 546/314; 546/316; 546/318; 546/339; 546/341; 546/342
[58] Field of Search .......... 546/339, 229, 546/314, 304, 290, 284.4, 286, 291, 341, 342, 316, 318; 504/244, 251, 254, 255, 260

[56] References Cited

U.S. PATENT DOCUMENTS

| | | |
|---|---|---|
| 3,555,031 | 1/1971 | Long et al. .......... 546/284.4 |
| 3,655,359 | 4/1972 | Krumkalns et al. .......... 504/244 |
| 4,631,081 | 12/1986 | Watson et al. .......... 546/286 |
| 4,808,722 | 2/1989 | Henrie, II .......... 546/292 |
| 4,826,531 | 5/1989 | Anthony et al. .......... 504/244 |
| 4,990,507 | 2/1991 | Takaya et al. .......... 546/306 |
| 5,278,133 | 1/1994 | Prisbylla .......... 504/244 |
| 5,284,956 | 2/1994 | Bachecker et al. .......... 546/339 |
| 5,310,919 | 5/1994 | Klausener et al. .......... 546/301 |
| 5,438,033 | 8/1995 | Drumm et al. .......... 504/130 |
| 5,595,958 | 1/1997 | Chen et al. .......... 504/250 |

FOREIGN PATENT DOCUMENTS

| | | |
|---|---|---|
| 0463 492 | 1/1992 | European Pat. Off. . |
| 4323 916 | 1/1995 | Germany . |

OTHER PUBLICATIONS

Chem. Abs., vol. 114; No. 11, Mel'Nikova et al, (Mar. 18, 1991).

Chem. Abs., vol. 125, No. 195679, Kleeman et al, (1996).

*Primary Examiner*—Deborah Lambkin
*Attorney, Agent, or Firm*—Keil & Weinkauf

[57] ABSTRACT

Substituted 2-phenylpyridines I

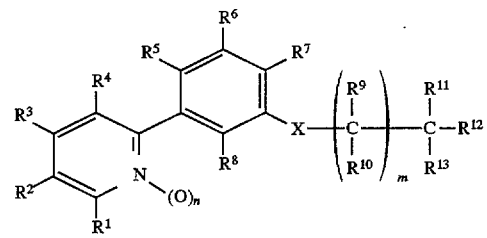

where substituents have the meaning described in the specification and their use as herbicides; for the desiccation/defoliation of plants.

11 Claims, No Drawings

SUBSTITUTED 2-PHENYLPIRIDINES

The present invention relates to novel substituted 2-phenylpyridines of the formula I

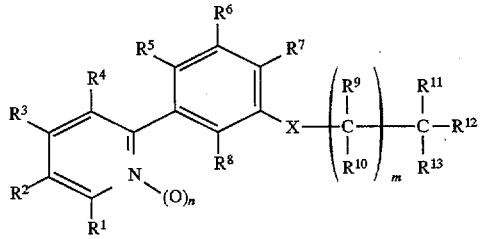

where the variables have the following meanings:

n is 0 or 1;

$R^1$, $R^3$ and $R^4$ independently of one another are hydrogen, halogen, $C_1$–$C_4$-alkyl, $C_1$–$C_4$-haloalkyl, hydroxyl, $C_1$–$C_4$-alkoxy, $C_1$–$C_4$-haloalkoxy, nitro, amino, $C_1$–$C_4$-alkyl-amino, di-($C_1$–$C_4$-alkyl)-amino, mercapto, $C_1$–$C_4$-alkylthio, $C_1$–$C_4$-haloalkylthio, cyano, carboxyl, aminocarbonyl, ($C_1$–$C_4$-alkylamino) carbonyl or di-($C_1$–$C_4$-alkyl)-aminocarbonyl;

$R^2$ is hydrogen, halogen, $C_1$–$C_4$-alkyl, $C_1$–$C_4$-haloalkyl, cyano, nitro, amino, hydroxyl, $C_1$–$C_4$-haloalkoxy, mercapto, $C_1$–$C_4$-alkylthio, $C_1$–$C_4$-haloalkylthio, $C_1$–$C_4$-alkylsulfinyl, $C_1$–$C_4$-haloalkylsulfinyl, $C_1$–$C_4$-alkylsulfonyl or $C_1$–$C_4$-halo-alkylsulfonyl;

$R^5$ is hydrogen, halogen or cyano;

$R^6$ and $R^8$ independently of one another are hydrogen or halogen;

$R^7$ is hydrogen, cyano, nitro, hydroxyl, trifluoromethylsulfonyloxy, halogen, $C_1$–$C_4$-alkyl, $C_1$–$C_4$-haloalkyl, $C_1$–$C_4$-alkoxy or $C_1$–$C_4$-haloalkoxy;

X is oxygen or sulfur, $R^9$ and $R^{10}$ independently of one another are hydrogen or $C_1$–$C_4$-alkyl;

m is 1, 2, 3 or 4;

$R^{11}$ is $C_1$–$C_6$-alkyl, $C_3$–$C_6$-cycloalkyl, Cl-$C_4$-haloalkyl having one to five halogen atoms, $C_2$–$C_4$-alkenyl, $C_2$–$C_4$-haloalkenyl having one to three halogen atoms, ($C_1$–$C_4$-alkoxy)carbonyl, ($C_1$–$C_4$-alkoxy)carbonyl-($C_1$–$C_4$-alkyl), unsubstituted or mono- to trisubstituted phenyl, unsubstituted or mono- or disubstituted thienyl, furanyl, tetrahydrofuranyl, pyrrolyl, oxazolyl, isoxazolyl, thiazolyl, isothiazolyl, pyridyl or pyrimidyl, where the substituents selected in each case are from the group consisting of nitro, cyano, halogen, $C_1$–$C_4$-alkyl and $C_1$–$C_4$-alkoxy;

$R^{12}$ and $R^{13}$ independently of one another are $C_1$–$C_4$-alkoxy or $C_1$–$C_4$-alkylthio or, together with the common carbon atom to which they are bonded, are the carbonyl group, a group

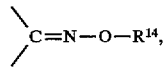

where $R^{14}$ is hydrogen, $C_1$–$C_4$-alkyl, $C_2$–$C_6$-alkenyl, $C_2$–$C_6$-haloalkenyl having one to three halogen atoms, ($C_1$–$C_4$-alkoxy)carbonyl-($C_1$–$C_4$-alkyl) or benzyl, or a heterocycle

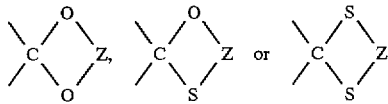

where Z is an ethylene or trimethylene chain in which, if desired, one to four hydrogen atoms can be substituted by $C_1$–$C_4$-alkyl or ($C_1$–$C_4$-alkoxy)carbonyl in each case, and the agriculturally utilizable salts of the compounds I, if these exist.

The invention additionally relates to the use of the compounds I as herbicides and/or for the desiccation/defoliation of plants, herbicidal compositions and compositions for the desiccation and/or defoliation of plants, which contain the compounds I as active substances, methods for the control of undesired vegetation and for the desiccation/defoliation of plants using the compounds I, and processes for preparing the compounds I and herbicidal compositions and compositions for the desiccation/defoliation of plants using the compounds I.

In the earlier German Application DE-A 43 23 916, inter alia, 2-phenylpyridines of the compound I type are described as herbicides and as compounds having desiccant/defoliant activity. Suitable choice of the substituents results, inter alia, in compounds of the formula II

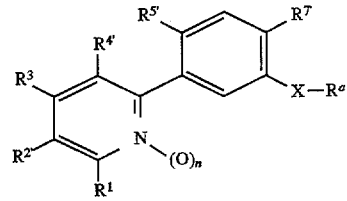

where $R^{2'}$ is halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_1$–$C_4$-haloalkylthio;

$R^{4'}$ is hydrogen, nitro, amino, cyano, hydroxyl, mercapto, hydroxycarbonyl, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-($C_1$–$C_4$-alkyl)-amino, $C_1$–$C_4$-alkylthio, $C_1$–$C_4$-haloalkylthio or ($C_1$–$C_4$-alkoxy)carbonyl;

$R^{5'}$ is hydrogen or halogen;

$R^{7'}$ is cyano, nitro, hydroxyl, halogen or trifluoromethyl;

$R^a$ is hydrogen or various organic radicals.

The herbicidal action of the known compounds with respect to the weeds, however, is not always completely satisfactory.

It is therefore an object of the present invention to provide novel herbicidally active compounds using which undesired plants can be specifically controlled better than previously.

The object also extends to the provision of novel compounds having desiccant/defoliant activity.

We have found that this object is achieved by the substituted 2-phenylpyridines of the formula I which are defined at the outset. Herbicidal compositions were further found which comprise the compounds I and have a very good herbicidal action. Processes for preparing these compositions and processes for controlling undesired vegetation using the compounds I were additionally found.

In addition, it was found that the compounds I are also suitable for the defoliation and desiccation of parts of plants, for which crop plants such as cotton, potato, rape, sunflower, soybean or field beans, in particular cotton, are suitable. With respect to this, compositions for the desiccation and/or defoliation of plants, processes for preparing these compositions and processes for the desiccation and/or defoliation of plants using the compounds I were found.

Depending on the substitution pattern, the compounds of the formula I can contain one or more centers of chirality and then exist as enantiomer or diastereomer mixtures. The invention relates both to the pure enantiomers or diastereomers and to their mixtures.

The substituted 2-phenylpyridines I can be present in the form of their agriculturally utilizable salts, where the nature of the salt generally does not matter. In general, the salts of those bases and those acid addition salts are suitable in which the herbicidal action is not adversely affected in comparison with the free compound I.

Suitable salts are particularly those of the alkali metals, preferably sodium and potassium salts, the alkaline earth metals, preferably calcium and magnesium salts, those of the transition metals, preferably zinc and iron salts, and also ammonium salts in which the ammonium ion, if desired, can carry one to four $C_1-C_4$-alkyl or hydroxy-$C_1-C_4$-alkyl substituents and/or a phenyl or benzyl substituent, preferably diisopropylammonium, tetramethylammonium, tetrabutylammonium, trimethylbenzylammonium and trimethyl (2-hydroxyethyl)ammonium salts, in addition phosphonium salts or sulfonium salts such as, preferably, tri($C_1-C_4$-alkyl)sulfonium salts, and sulfoxonium salts such as, preferably, tri($C_1-C_4$-alkyl) sulfoxonium salts.

The acid addition salts which may be mentioned are primarily the hydrochlorides and hydrobromides, sulfates, nitrates, phosphates, oxalates and the dodecylbenzenesulfonates.

The names alkyl, haloalkyl, alkoxy, haloalkoxy, alkylthio, haloalkylthio, alkylamino, dialkylamino, alkylaminocarbonyl, dialkylaminocarbonyl, alkylsulfinyl, haloalkylsulfinyl, alkylsulfonyl, haloalkylsulfonyl, alkenyl, haloalkenyl, alkoxycarbQnyl, alkoxycarbonylalkyl and cycloalkyl used in the definition of the substituents $R^1$ to $R^{14}$ are, like the meaning halogen, collective terms for individual lists of the separate group members. All carbon chains, ie. all alkyl, haloalkyl, alkenyl and haloalkenyl moieties, can be straight-chain or branched. Halogenated substituents preferably carry one to five identical or different halogen atoms.

Specific examples are:

halogen: fluorine, chlorine, bromine or iodine;

$C_1-C_4$-alkyl and the alkyl moiety of ($C_1-C_4$-alkoxy) carbonyl-($C_1-C_4$-alkyl): methyl, ethyl, n-propyl, 1-methylethyl, n-butyl, 1-methylpropyl, 2-methylpropyl or 1,1-dimethylethyl;

$C_1-C_6$-alkyl: $C_1-C_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl;

$C_1-C_4$-haloalkyl: a $C_1-C_4$-alkyl radical such as mentioned above, which is partially or completely substituted by fluorine, chlorine, bromine and/or iodine, ie., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1-C_4$-alkoxy: methoxy, ethoxy, n-propoxy, 1-methylethoxy, n-butoxy, 1-methylpropoxy, 2-methylpropoxy or 1,1-dimethylethoxy;

$C_1-C_4$-haloalkoxy: $C_1-C_4$-alkoxy as mentioned above, which is partially or completely substituted by fluorine, chlorine, bromine and/or iodine, ie., for example, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

($C_1-C_4$-alkoxy)carbonyl and the alkoxycarbonyl moiety of ($C_1-C_4$-alkoxy)carbonyl-($C_1-C_4$-alkyl): methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl or 1,1-dimethylethoxycarbonyl;

$C_1-C_4$-alkylthio: methylthio, ethylthio, n-propylthio, 1-methylethylthio, n-butylthio, 1-methylpropylthio, 2-methylpropylthio or 1,1-dimethylethylthio;

$C_1-C_4$-haloalkylthio: $C_1-C_4$-alkylthio as mentioned above, which is partially or completely substituted by fluorine, chlorine, bromine and/or iodine, ie., for example, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_4$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl or 1,1-dimethylethylsulfinyl;

$C_1$–$C_4$-haloalkylsulfinyl: $C_1$–$C_4$-alkylsulfinyl as mentioned above, which is partially or completely substituted by fluorine, chlorine, bromine and/or iodine, ie., for example, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl or nonafluorobutylsulfinyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl or 1,1-dimethylethylsulfonyl;

$C_1$–$C_4$-haloalkylsulfonyl: $C_1$–$C_4$-alkylsulfonyl as mentioned above, which is partially or completely substituted by fluorine, chlorine, bromine and/or iodine, i.e., for example, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2,2,2-trichloroethylsulfonyl, 2-chloro-2-fluoroethylsulfonyl, 2-chloro-2,2-difluoroethylsulfonyl, 2,2-dichloro-2-fluoroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2bromoethylsulfonyl, 4-fluorobutylsulfonyl, 4-chlorobutylsulfonyl, 4-bromobutylsulfonyl or nonafluorobutylsulfonyl;

$C_1$–$C_4$-alkylamino and the alkylamino moiety of ($C_1$–$C_4$-alkylamino) carbonyl: methylamino, ethylamino, n-propylamino, 1-methylethylamino, n-butylamino, 1-methylpropylamino, 2-methylpropylamino or 1,1-dimethylethylamino;

di-($C_1$–$C_4$-alkyl)amino and the dialkylamino moiety of di-($C_1$–$C_4$-alkyl)aminocarbonyl: e.g. N,N-dimethylamino, N,N-diethylamino, N,N-diisopropylamino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino;

$C_3$–$C_6$-cycloalkyl: cyclopropyl, cyclobutyl, cyclopentyl or cyclohexyl;

$C_2$–$C_4$-alkenyl: ethenyl, prop-1-en-1-yl, prop-2-en-1-yl, 1-methylethenyl, n-buten-1-yl, n-buten-2-yl, n-buten-3-yl, 1-methyl-prop-1-en-1-yl, 2-methyl-prop-1-en-1-yl, 1-methyl-prop-2-en-1-yl or 2-methyl-prop-2-en-1-yl;

$C_2$–$C_6$-alkenyl: $C_2$–$C_4$-alkenyl as mentioned above, and also, for example, n-penten-1-yl, n-penten-2-yl, n-penten-3-yl, n-penten-4-yl, 1-methyl-but-1-en-1-yl, 2-methyl-but-1-en-1-yl, 3-methyl-but-1-en-1-yl, 1-methyl-but-2-en-1-yl, 2-methyl-but-2-en-1-yl, 3-methyl-but-2-en-1-yl, 1-methyl-but-3-en-1-yl, 2-methyl-but-3-en-1-yl, 3-methyl-but-3-en-1-yl, 1,1-dimethyl-prop-2-en-1-yl, 1,2-dimethyl-prop-1-en-1-yl, 1,2-dimethyl-prop-2-en-1-yl, 1-ethyl-prop-1-en-2-yl, 1-ethyl-prop-2-en-1-yl, n-hex-1-en-1-yl, n-hex-2-en-1-yl, n-hex-3-en-1-yl, n-hex-4-en-1-yl, n-hex-5-en-1-yl, 1-methyl-pent-1-en-1-yl, 2-methyl-pent-1-en-1-yl, 3-methyl-pent-1-en-1-yl, 4-methyl-pent-1-en-1-yl, 1-methyl-pent-2-en-1-yl, 2-methyl-pent-2-en-1-yl, 3-methyl-pent-2-en-1-yl, 4-methyl-pent-2-en-1-yl, 1-methyl-pent-3-en-1-yl, 2-methyl-pent-3-en-1-yl, 3-methyl-pent-3-en-1-yl, 4-methyl-pent-3-en-1-yl, 1-methyl-pent-4-en-1-yl, 2-methyl-pent-4-en-1-yl, 3-methyl-pent-4-en-1-yl, 4-methyl-pent-4-en-1-yl, 1,1-dimethyl-but-2-en-1-yl, 1,1-dimethyl-but-3-en-1-yl, 1,2-dimethyl-but-2-en-1-yl, 1,2-dimethyl-but-2-en-1-yl, 1,2-dimethyl-but-3-en-1-yl, 1,3-dimethyl-but-2-en-1-yl, 1,3-dimethyl-but-2-en-1-yl, 1,3-dimethyl-but-3-en-1-yl, 2,2-dimethyl-but-3-en-1-yl, 2,3-dimethyl-but-3-en-1-yl, 2,3-dimethyl-but-2-en-1-yl, 2,3-dimethyl-but-3-en-1-yl, 3,3-dimethyl-but-3-en-1-yl, 3,3-dimethyl-but-2-en-1-yl, 1-ethyl-but-1-en-1-yl, 2-ethyl-but-2-en-1-yl, 1-ethyl-but-3-en-1-yl, 2-ethyl-but-1-en-1-yl, 2-ethyl-but-2-en-1-yl, 2-ethyl-but-3-en-1-yl, 1,1,2-trimethyl-prop-2-en-1-yl, 1-ethyl-1-methyl-prop-2-en-1-yl, 1-ethyl-2-methyl-prop-1-en-1-yl or 1-ethyl-2-methyl-prop-2-en-1-yl;

$C_2$–$C_4$-haloalkenyl: $C_2$–$C_4$-alkenyl as mentioned above, which is partially or completely substituted by fluorine, chlorine, bromine and/or iodine, ie., for example, 2-chloroallyl, 3-chloroallyl or 3,3-dichloroallyl;

$C_2$–$C_6$-Haloalkenyl: $C_2$–$C_6$-alkenyl as mentioned above, which is partially or completely substituted by fluorine, chlorine, bromine and/or iodine, ie., for example, 1-chlorovinyl, 2-chlorovinyl, 2,2-dichlorovinyl, 1,2,3-trichlorovinyl, 2-chloroallyl, 3-chloroallyl or 3,3-dichloroallyl.

The phenyl ring and the heterocyclic rings in the definition of $R^{11}$ are preferably substituted or carry a halogen, methyl or methoxy substituent.

With respect to the use of the compounds of the formula I according to the invention as herbicides and/or as active compounds having defoliant/desiccant activity, the variables preferably have the following meanings, namely in each case per se or in combination:

n is zero;

$R^1$, $R^3$ and $R^4$ independently of one another are hydrogen or halogen;

$R^2$ is halogen or $C_1$–$C_4$-haloalkyl having one to five halogen atoms;

$R^5$ is hydrogen or halogen, in particular fluorine;

$R^6$ and $R^8$ are hydrogen;

$R^7$ is cyano or halogen, in particular cyano or chlorine;

X is oxygen;

$R^9$ and $R^{10}$ independently of one another are hydrogen or $C_1$–$C_4$-alkyl;

m is one or two;

$R^{11}$ is $C_1$–$C_6$-alkyl or $C_3$–$C_6$-cycloalkyl;

$R^{12}$ and $R^{13}$, together with the common carbon atom to which they are bonded, are the carbonyl group.

Particularly preferred compounds are the compounds Ia (=I where n=0; $R^1$, $R^3$, $R^{6'}$ $R^8$ and $R^{10}$=hydrogen; $R^2$=$CF_3$; $R^4$=chlorine; $R^{11}$=methyl; $R^{12}$ and $R^{13}$, together with the common C atom=carbonyl) listed in Table 1 below:

TABLE 1

| No. | $R^5$ | $R^7$ | X | $R^9$ | m | physical data |
|---|---|---|---|---|---|---|
| Ia.01 | H | Cl | O | H | 1 | |
| Ia.02 | H | Cl | O | H | 2 | |
| Ia.03 | H | Cl | O | $CH_3$ | 1 | |
| Ia.04 | H | Cl | O | $CH_3$ | 2 | |
| Ia.05 | H | Cl | S | H | 1 | |
| Ia.06 | H | Cl | S | H | 2 | |
| Ia.07 | H | Cl | S | $CH_3$ | 1 | |
| Ia.08 | H | Cl | S | $CH_3$ | 2 | |
| Ia.09 | H | CN | O | H | 1 | see Preparation Example 1 |
| Ia.10 | H | CN | O | H | 2 | |
| Ia.11 | H | CN | O | $CH_3$ | 1 | |
| Ia.12 | H | CN | O | $CH_3$ | 2 | |
| Ia.13 | H | CN | S | H | 1 | |
| Ia.14 | H | CN | S | H | 2 | |
| Ia.15 | H | CN | S | $CH_3$ | 1 | |
| Ia.16 | H | CN | S | $CH_3$ | 2 | |
| Ia.17 | F | Cl | O | H | 1 | |
| Ia.18 | F | Cl | O | H | 2 | |
| Ia.19 | F | Cl | O | $CH_3$ | 1 | |
| Ia.20 | F | Cl | O | $CH_3$ | 2 | |
| Ia.21 | F | Cl | S | H | 1 | |
| Ia.22 | F | Cl | S | H | 2 | |
| Ia.23 | F | Cl | S | $CH_3$ | 1 | |
| Ia.24 | F | Cl | S | $CH_3$ | 2 | |
| Ia.25 | F | CN | O | H | 1 | |
| Ia.26 | F | CN | O | H | 2 | |
| Ia.27 | F | CN | O | $CH_3$ | 1 | |
| Ia.28 | F | CN | O | $CH_3$ | 2 | |
| Ia.29 | F | CN | S | H | 1 | |
| Ia.30 | F | CN | S | H | 2 | |
| Ia.31 | F | CN | S | $CH_3$ | 1 | |
| Ia.32 | F | CN | S | $CH_3$ | 2 | |

In addition, the following substituted 2-phenylpyridines of the formula I are particularly preferred:

the compounds Ib.01–Ib.32 which differ from the corresponding compounds Ia.01–Ia.32 only in that $R^{11}$ is ethyl:

the compounds Ic.01–Ic.32 which differ from the corresponding compounds Ia.01–Ia.32 only in that $R^{11}$ is n-propyl:

the compounds Id.01–Id.32 which differ from the corresponding compounds Ia.01–Ia.32 only in that $R^{11}$ is isopropyl:

the compounds Ie.01–Ie.32 which differ from the corresponding compounds Ia.01–Ia.32 only in that $R^{11}$ is n-butyl:

the compounds If.01–If.32 which differ from the corresponding compounds Ia.01–Ia.32 only in that $R^{11}$ is 2-methylpropyl:

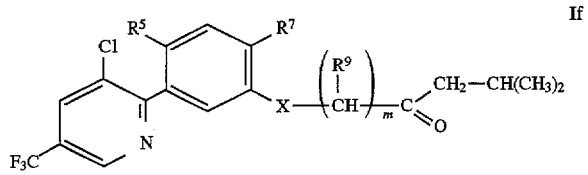

the compounds Ig.01–Ig.32 which differ from the corresponding compounds Ia.01–Ia.32 only in that $R^{11}$ is tert-butyl:

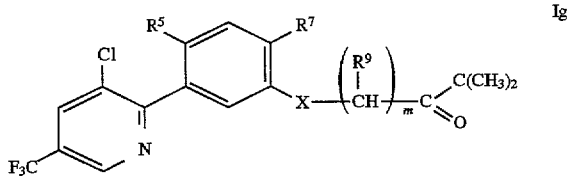

the compounds Ih.01–Ih.32 which differ from the corresponding compounds Ia.01–Ia.32 only in that $R^{11}$ is cyclopropyl:

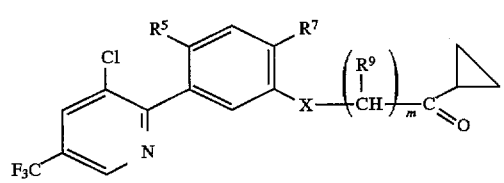

the compounds Ii.01–Ii.32 which differ from the corresponding compounds Ia.01–Ia.32 only in that $R^{11}$ is methoxycarbonylmethyl:

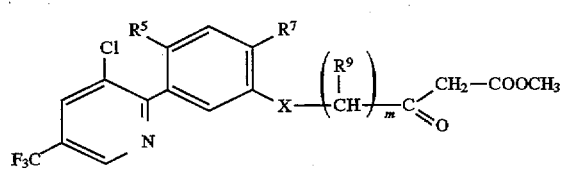

the compounds Ik.01–Ik.32 which differ from the corresponding compounds Ia.01–Ia.32 only in that $R^{11}$ is ethoxycarbonylmethyl:

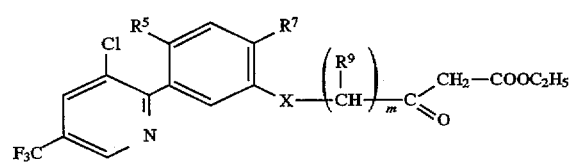

Particularly preferred compounds are additionally the compounds I1 (=I where n=0; $R^1$, $R^3$, $R^6$, $R^8$ and $R^{10}$= hydrogen; $R^2$=$CF_3$; $R^4$=chlorine; m=1; $R^{11}$=methyl; $R^{12}$ and $R^{13}$=methoxy) listed in Table 2 below:

TABLE 2

II

| No. | $R^5$ | $R^7$ | X | $R^9$ | physical data |
|---|---|---|---|---|---|
| I1.01 | H | Cl | O | H | |
| I1.02 | H | Cl | O | $CH_3$ | |
| I1.03 | H | Cl | S | H | |
| I1.04 | H | Cl | S | $CH_3$ | |
| I1.05 | H | CN | O | H | |
| I1.06 | H | CN | O | $CH_3$ | |
| I1.07 | H | CN | S | H | |
| I1.08 | H | CN | S | $CH_3$ | |
| I1.09 | F | Cl | O | H | |
| I1.10 | F | Cl | O | $CH_3$ | |
| I1.11 | F | Cl | S | H | |
| I1.12 | F | Cl | S | $CH_3$ | |
| I1.13 | F | CN | O | H | |
| I1.14 | F | CN | O | $CH_3$ | |
| I1.15 | F | CN | S | H | |
| I1.16 | F | CN | S | $CH_3$ | |

Finally, the substituted 2-phenylpyridines I below are additionally particularly preferred:

the compounds Im.01–Im.16 which differ from the corresponding compounds I1.01–I1.16 only in that $R^{12}$ and $R^{13}$ are ethoxy:

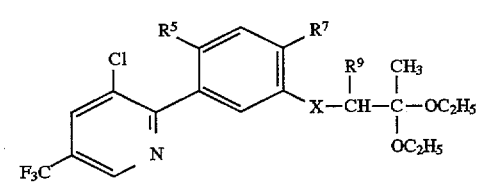

the compounds In.01–In.16 which differ from the corresponding compounds I1.01–I1.16 only in that $R^{12}$ and $R^{13}$, together with the common C atom to which they are bonded, form a 1,3-dioxolane ring:

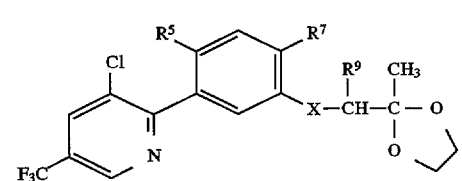

the compounds Io.01–Io.16 which differ from the corresponding compounds I1.01–I1.16 only in that $R^{12}$ and $R^{13}$, together with the common C atom to which they are bonded, form a 1,3-dioxane ring:

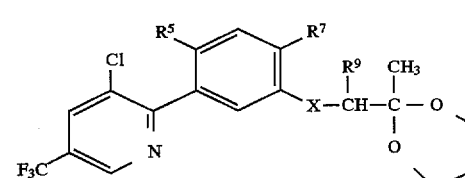

the compounds Ip.01–Ip.16 which differ from the corresponding compounds I1.01–I1.16 only in that $R^{12}$ and $R^{13}$, together with the common C atom to which they are bonded, form a 1,3-dithiolane ring:

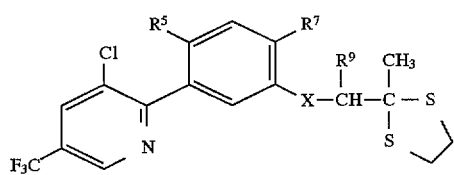

the compounds Iq.01–Iq.16 which differ from the corresponding compounds Il.01–Il.16 only in that $R^{12}$ and $R^{13}$, together with the common C atom to which they are bonded, form a 1,3-dithiane ring:

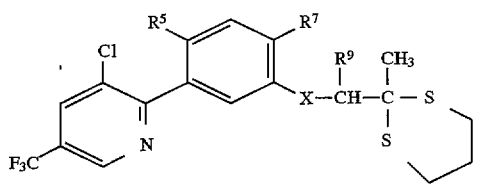

the compounds Ir.01–Ir.16 which differ from the corresponding compounds Il.01–Il.16 only in that $R^{12}$ and $R^{13}$, together with the common C atom to which they are bonded, form a

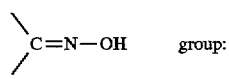

group:

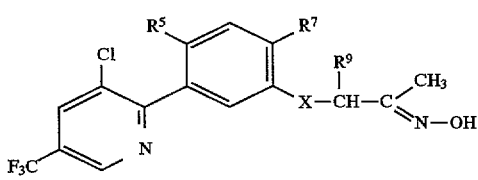

the compounds Is.01–Is.16 which differ from the corresponding compounds Il.01–Il.16 only in that $R^{12}$ and $R^{13}$, together with the common C atom to which they are bonded, form a

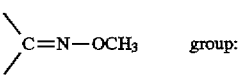

group:

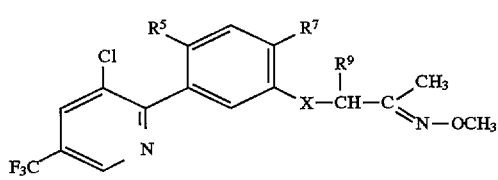

the compounds It.01–It.16 which differ from the corresponding compounds Il.01–Il1.32 only in that $R^{12}$ and $R^{13}$, together with the common C atom to which they are bonded, form a

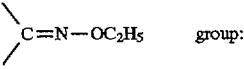

group:

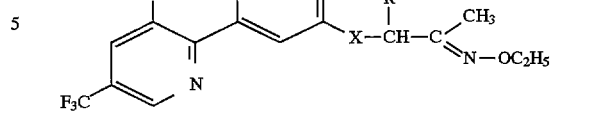

The substituted 2-phenylpyridines of the formula I are obtainable in various ways, for example by one of the following processes:

Process A

Alkylation of 3-pyridylphenols or 3-pyridylthiophenols III with alkylating agents IV in the presence of a base

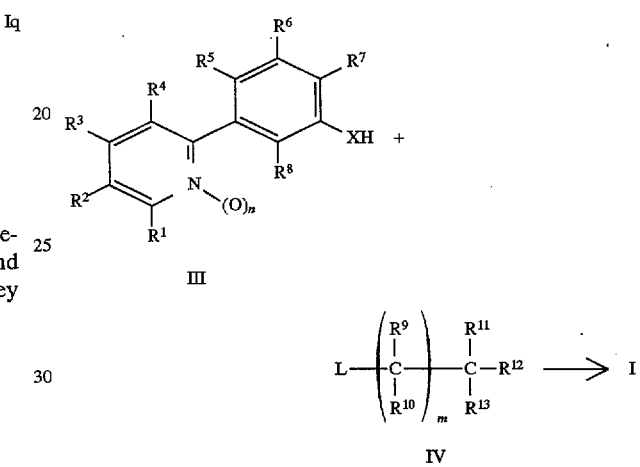

L is chlorine, bromine, iodine, methylsulfonyloxy, trifluoromethylsulfonyloxy, phenylsulfonyloxy or p-tolylsulfonyloxy.

Generally the reaction is carried out in an inert solvent or diluent which is preferably aprotic, ie., for example, in N,N-dimethylformamide, dimethyl sulfoxide, acetone, N-methylpyrrolidone, acetonitrile or in an ether such as diethyl ether, tetrahydrofuran or 1,4-dioxane.

Bases which can be used are, for example, alkali metal carbonates and hydrogen carbonates such as sodium hydrogen carbonate, potassium hydrogen carbonate, sodium carbonate and potassium carbonate, alkali metal alkoxides such as sodium methoxide and potassium tert-butoxide, alkali metal hydroxides such as sodium hydroxide, and alkali metal hydrides such as sodium hydride.

Further details for carrying out alkylation reactions of this type are to be found, for example, in the following literature:

C. D. Hurd and P. Perletz, J. Am. Chem. Soc. 68 (1946), 38;

W. M. Best and D. Wege, Aust. J. Chem. 39 (1986), 647;

D. Salunkhe et al., Acta Chim. Hung. 124 (1987), 411;

D. D. Weller et al., J. Org. Chem. 48 (1983), 3061;

J. E. Banfield et al., J. Chem. Soc. (1956), 4791;

P. S. Kukolja et al., J. Med. Chem. 28 (1985), 1886;

K. Goerlitzer et al., Arch. Pharm. 313 (1980), 27;

A. Shafiee et al., J. Het. Chem. 19 (1982), 1305;

E. Campaigne and S. Kim Chung, J. Het. Chem. 20 (1983), 1697;

S. Apparao and R. R. Schmidt, Synthesis 1987, 896.

Process B

Reaction of substituted 2-phenylpyridines I in which $R^{12}$ and $R^{13}$, together with the common carbon atom to which they are bonded, are the carbonyl group, either with hydroxylamine, it then being possible to alkylate the product, or with an alkoxyamine $H_2N—O—R^{14}$:

P. H. H. Hermkens et al., Tetrahedron 46 (1990), 833;

E. V. Dehmlow et al., Chem. Ber. 119 (1986), 2956;

R. Plate et al., J. Chem. Soc. Perkin Trans. 1 (1987), 2478–2480;

Y. Tsuda et al., Heterocycles 27 (1988), 63;

J. Koyama et al., Heterocycles 29 (1989), 1649.

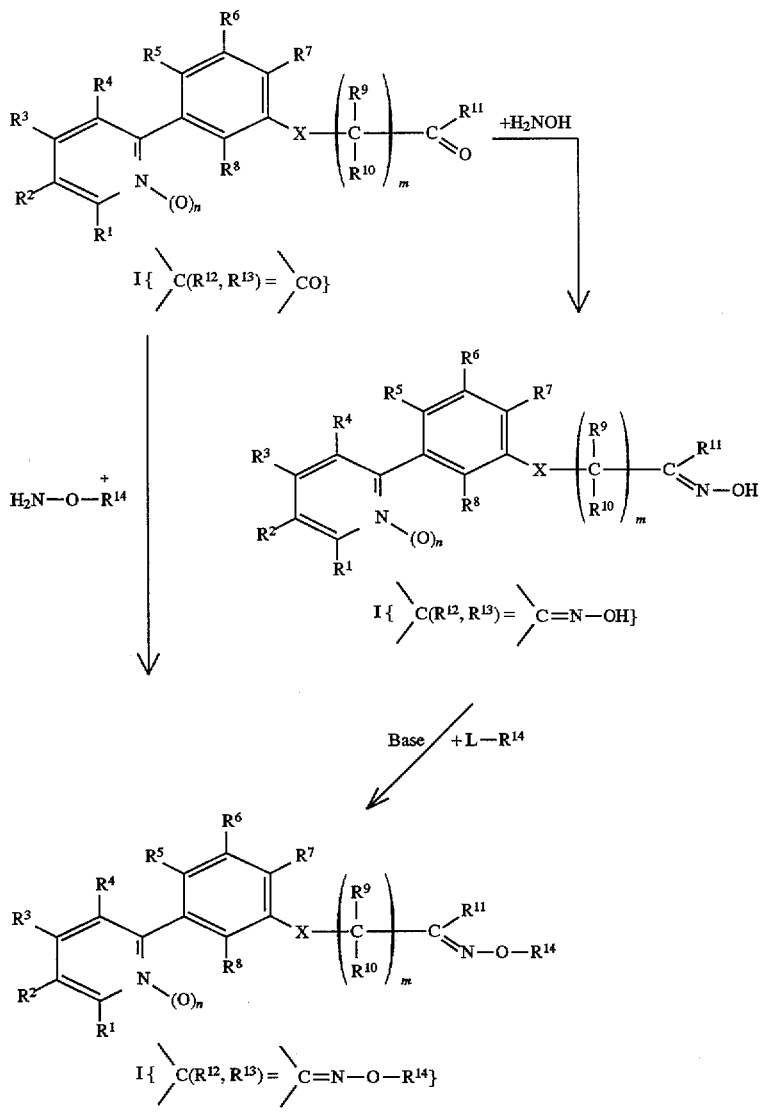

For definition of L see Process A.

The process conditions for reactions of ketones with hydroxylamine (derivatives) of this type can be taken, for example, from the following literature:

N. Bodor et al., J. Med. Chem. 21 (1988), 100;

N. Latif et al., Indian J. Chem. B19, No. 4 (1980), 301–304;

M. Watanabe et al., Chem. and Pharm. Bull. 32 (1984), 3551;

Process C

Reaction of substituted 2-phenylpyridines I in which $R^{12}$ and $R^{13}$, together with the common carbon atom to which they are bonded, are the carbonyl group, in the presence of an acid, either with dihydric alcohols or thioalcohols or with monohydric alcohols or thioalcohols or with ortho(thio) esters. The products I where $R^{12}$ and $R^{13}$=alkoxy or alkylthio can be transacetalated, if desired, in the presence of an acid:

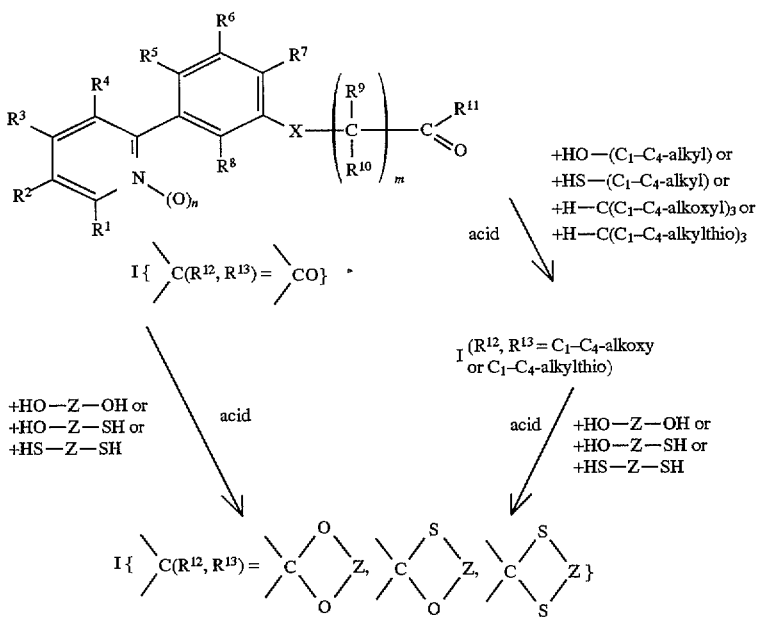

Further details for carrying out ketal formation reactions of this type are to be found in the following literature, to which reference is made by way of example:

D. J. Collins and J. J. Hobbs, Chem. Ind. (1964), 1063;

C. E. Ballov, Biochem. Prep. (1960), 45;

C. L. Stevens and A. E. Sherr, J. Org. Chem. 17 (1952), 1228;

J. L. Reymond and P. Vogel, J. Chem. Soc. Chem. Commun. 16 (1990), 1070;

K. C. Nicolaov et al., Angew. Chem. Int. Ed. 30 (1991), 299;

V. Rosnati et al., Gazz. Chim. Ital. 94 (1964), 767;

W. M. Best und D. Wege, Aust. J. Chem. 39 (1986), 647;

F. Kido et al., J. Chem. Soc. Chem. Commun. 8 (1986), 590;

M. T. Barros et al., Tetrahedron 44 (1988), 2283;

L. L. Melhado und J. L. Brodsky, J. Org. Chem. 53 (1988), 3852.

Process D

Oxidation of substituted 2-phenylpyridines of the formula I in which n is zero, in a manner known per se {cf., for example, A. Albini and S. Pietra, Heterocyclic N-Oxides, CRC Press Inc., Boca Raton, USA 1991; H. S. Mosher et al., Org. Synth. Coll. Vol. IV 1963, page 828; E. C. Taylor et al., Org. Synth. Coll. Vol. IV 1963, page 704; T. W. Bell et al., Org. Synth. 69 (1990), 226}:

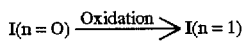

Among the oxidants customary for the oxidation of the pyridine ring, reference may be made by way of example to peracetic acid, trifluoroperacetic acid, perbenzoic acid, m-chloroperbenzoic acid, monopermaleic acid, magnesium monoperphthalate, sodium perborate, Oxone® (contains peroxydisulfate), pertungstic acid and hydrogen peroxide.

Suitable solvents are, for example, water, sulfuric acid, carboxylic acids such as acetic acid and trifluoroacetic acid, and halogenated hydrocarbons such as dichloromethane and chloroform.

Normally, the oxidation takes place at from 0° C. to the boiling point of the reaction mixture.

The oxidant is normally employed in at least equimolar amounts, based on the starting compound. In general, an excess of oxidant has proven particularly advantageous.

If not stated otherwise, all processes described above are expediently performed at atmospheric pressure or under the autogenous pressure of the respective reaction mixture.

The reaction mixtures are generally worked up by methods known per se, for example by removing the solvent, partitioning the residue in a mixture of water and a suitable organic solvent and working up the organic phase to the product.

The substituted 2-phenylpyridines of the formula I can contain one or more centers of chirality and are then customarily obtained as enantiomer or diastereomer mixtures. If desired, the mixtures can be separated into the largely pure isomers by the methods which are customary for this purpose, e.g. by means of crystallization or chromatography on an optically active adsorbate. Pure optically active isomers can also be prepared, for example, from corresponding optically active starting materials.

Substituted 2-phenylpyridines I containing CH-acidic substituents can be converted in a manner known per se into their salts, preferably into their alkali metal salts.

Salts of I whose metal ion is not an alkali metal ion can be prepared in a customary manner by double decomposition of the corresponding alkali metal salts, just as ammonium and phosphonium salts can be prepared by means of ammonia, phosphonium, sulfonium or sulfoxonium hydroxides.

Compounds I which carry a terminal amino group can further form acid addition salts. Suitable salts are generally the salts of those acids which also do not adversely affect the herbicidal or desiccant/defoliant action of I, ie., for example, the hydrochlorides and hydrobromides, sulfates, nitrates, phosphates, oxalates or the dodecylbenzenesulfonates.

The compounds I and their agriculturally utilizable salts are suitable as herbicides, both as isomer mixtures and in the form of the pure isomers. The herbicidal compositions comprising I control vegetation on noncultivated areas very effectively, particularly at high application rates. They act against broad-leaved weeds and grass weeds in crops such as wheat, rice, maize, soybeans and cotton without noticeably damaging the crop plants. This effect occurs especially at low application rates.

Depending on the particular application method, the compounds I or herbicidal compositions containing them can additionally be employed in a further number of crop plants for eliminating undesired plants. Suitable crops, for example, are the following:

*Allium cepa, Ananas comosus, Arachis hypogaea, Asparagus officinalis, Beta vulgaris* spp. *altissima, Beta vulgaris* spp. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum,(Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum (N. rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestre, Ricinus communis, Saccharum officinarum, Secale cereale, Solanum tuberosum, Sorghum bicolor (S. vulgare), Theobroma cacao, Trifolium pratense, Triticum aestivum, Triticum durum, Vicia faba, Vitis vinifera, Zea mays.*

Moreover, the compounds I can also be employed in crops which are tolerant to the action of herbicides as a result of breeding, including genetic engineering methods.

In addition, the substituted 2-phenylpyridines I are also suitable for the desiccation and/or defoliation of plants.

As desiccants, they are in particular suitable for the desiccation of the above-ground parts of crop plants such as potato, rape, sunflower and soybean. Completely mechanized harvesting of these important crop plants is thus made possible.

Of economic interest is also the facilitation of harvesting, which is made possible by the temporally concentrated decrease or reduction in the power of adhesion to the tree in the case of citrus fruits, olives or in the case of other species and varieties of pomes, drupes and indehiscent fruit. The same mechanism, that is the promotion of the formation of separating tissue between fruit or leaf and stem part of the plants is also essential for a highly controllable defoliation of useful plants, in particular cotton.

Additionally, the shortening of the time interval in which the individual cotton plants become ripe leads to an enhanced fiber quality after harvesting.

The compounds I or the compositions containing them can be applied by spraying, atomizing, dusting, broadcasting or watering, for example in the form of directly sprayable aqueous solutions, powders, suspensions, also high-percentage aqueous, oily or other suspensions or dispersions, emulsions, oil dispersions, pastes, dusting compositions, broadcasting compositions or granules. The application forms depend entirely on the intended uses; in each case if possible, they should guarantee the finest dispersion of the active compounds according to the invention.

Suitable inert auxiliaries are essentially: mineral oil fractions of medium to high boiling point such as kerosene and diesel oil, also coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone and water.

Aqueous application forms can be prepared from emulsion concentrates, suspensions, pastes, wettable powders or water-dispersible granules by addition of water. For the production of emulsions, pastes or oil dispersions, the substances as such or dissolved in an oil or solvent can be homogenized in water by means of wetting agents, adherents, dispersants or emulsifiers. However, concentrates consisting of active substance, wetting agent, adherent, dispersant or emulsifier and possibly solvents or oil can also be prepared, which are suitable for dilution with water.

Suitable surface-active substances (adjuvants) are the alkali metal, alkaline earth metal or ammonium salts of aromatic sulfonic acids, e.g. lignosulfonic acid, phenolsulfonic acid, naphthalenesulfonic acid and dibutylnaphthalenesulfonic acid, as well as of fatty acids, alkyl- and alkylarylsulfonates, alkyl-, lauryl ether and fatty alcohol sulfates, and also salts of sulfated hexa-, hepta- and octadecanols, as well as of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenyl ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignin-sulfite waste liquors or methylcellulose.

Powder, broadcasting and dusting compositions can be produced by mixing or joint grinding of the active substances with a solid carrier.

Granules, e.g. coated, impregnated and homogeneous granules can be produced by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products such as cereal meal, tree bark, wood and nut-shell meal, cellulose powder or other solid carriers.

The concentrations of the active compounds I in the ready-to-apply preparations can be varied within wide ranges. In general, the formulations contain from 0.001 to 98% by weight, preferably from 0.01 to 95% by weight, of active compound. The active compounds are in this case employed in a purity of from 90% to 100%, preferably from 95% to 100% (according to NMR spectrum).

The following formulation examples illustrate the preparation of such preparations:

I. 20 parts by weight of the compound No. Ia.09 are dissolved in a mixture which consists of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid and 5 parts by weight of the addition product of 40 mol of ethylene oxide to 1 mol of castor oil. By pouring the solution out and finely dispersing it in 100,000 parts by weight of water, an aqueous dispersion is obtained which contains 0.02% by weight of the active compound;

II. 20 parts by weight of the compound No. Ih.09 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound;

III. 20 parts by weight of the active compound No. Ia.09 are dissolved in a mixture which consists of 25 parts by weight of cyclohexanone, 65 parts by weight of a mineral oil fraction of boiling point 210° to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound;

IV. 20 parts by weight of the active compound No. Ih.09, 3 parts by weight of the sodium salt of diisobutylnaphthalene-α-sulfonic acid, 17 parts by weight of the sodium salt of a lignosulfonic acid from a sulfite waste liquor and 60 parts by weight of powdered silica gel are mixed well and ground in a hammer mill. By finely dispersing the mixture in 20,000 parts by weight of water, a spray liquor is obtained which contains 0.1% by weight of the active compound;

V. 3 parts by weight of the active compound No. Ia.09 are mixed with 97 parts by weight of finely divided kaolin. A dusting composition is obtained in this manner which contains 3% by weight of the active compound;

VI. 20 parts by weight of the active compound No. Ih.09 are intimately mixed with 2 parts by weight of the calcium salt of dodecylbenzenesulfonic acid, 8 parts by weight of fatty alcohol polyglycol ether, 2 parts by weight of the sodium salt of a phenol-urea-formaldehyde condensate and 68 parts by weight of a paraffinic mineral oil. A stable oily dispersion is obtained.

VII. 1 part by weight of the compound No. Ia.09 is dissolved in a mixture which consists of 70 parts by weight of cyclohexanone, 20 parts by weight of ethoxylated isooctylphenol and 10 parts by weight of ethoxylated castor oil. A stable emulsion concentrate is obtained.

VIII. 1 part by weight of the compound No. Ih.09 is dissolved in a mixture which consists of 80 parts by weight of cyclohexanone and 20 parts by weight of Emulphor EL[1]. A stable emulsion concentrate is obtained.

[1] ethoxylated castor oil

The application of the active compounds I or of the herbicidal compositions can be carried out pre-emergence or post-emergence. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rates of active compound I are, depending on the target to be controlled, time of year, target plants and stage of growth from 0.001 to 3.0, preferably from 0.01 to 1 kg/ha of active substance (a.s.).

For widening the spectrum of action and for achieving synergistic effects, the substituted 2-phenylpyridines I can be mixed with numerous representatives of other herbicidal or growth-regulating active compound groups and applied together. For example, suitable mixture components are 1,2,4-thiadiazoles, 1,3,4-thiadiazoles, amides, aminophosphoric acid and its derivatives, aminotriazoles, anilides, aryloxy-/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracius, imidazoles, imidazolinones, N-phenyl-3,4,5,6-tetrahydrophthalimides, oxadiazoles, oxiranes, phenols, aryloxy- and heteroaryloxyphenoxypropionic acid esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboximades and uracils.

It may additionally be of use to apply the compounds I on their own or, in combination with other herbicides, jointly, additionally mixed with further plant protection compositions, for example with compositions for controlling pests or phytopathogenic fungi or bacteria. Additionally of interest is the miscibility with mineral salt solutions, which are employed for the elimination of nutritional and trace element deficiencies. Non-phytotoxic oils and oil concentrates can also be added.

PREPARATION EXAMPLES

Example 1

3-Chloro-2-(4-cyano-3-(2-oxopropoxy)phenyl)-5-trifluoromethyl-pyridine (No. Ia.09)

1.5 g of 3-chloro-2-(4-cyano-3-hydroxyphenyl)-5-trifluoromethyl-pyridine, 1.0 g of chloroacetone, 1.5 g of potassium carbonate, 0.8 g of sodium iodide and 200 ml of acetone were refluxed for 8 hours. The reaction mixture was then concentrated, after which the residue was stirred in 20 ml of water. The insoluble portion was separated off and washed well with water. The crude product was then stirred in succession with n-hexane and with ether. After drying in a vacuum drying oven, 0.4 g of white crystals having a melting point of 146°–147° C. were finally obtained. Yield: 22%.

Precursor α

3-Chloro-2-(4-cyano-3-methoxyphenyl)-5-trifluoromethylpyridine 31 ml of a 30% strength by weight solution of sodium methoxide in methanol were added to a solution of 49.0 g of 3-chloro-2-(4-cyano-3-nitrophenyl-5-trifluoromethylpyridine (disclosed in DE-A 43 23 916) in 500 ml of anhydrous methanol. After refluxing for 6 hours, the reaction mixture was allowed to stand for 16 hours at 23° C., after which the crystals formed in the meantime were separated off, washed with a little methanol and finally dried in a vacuum drying oven. Yield: 33.3 g (71%) of white crystals having a melting point of 135°–137° C.

Precursor β

3-Chloro-2-(4-cyano-3-hydroxyphenyl)-5-trifluoromethylpyridine 5.0 g of 3-chloro-2-(4-cyano-3-methoxyphenyl)-5-trifluoromethylpyridine and 5.5 g of pyridine hydrochloride were stirred for 2 hours at 200° C. After cooling, the reaction mixture was thoroughly stirred with 100 ml of water. The solid portion was then separated off and purified by means of column chromatography on silica gel (cyclohexane/methyl tert-butyl ether (2:1) as eluent). Yield: 3.4 g (71%) of white crystals having a melting point of 155°–157° C.

$^1$H-NMR (250 MHz, in d$^6$-dimethyl sulfoxide): δ [ppm] =7.28(d,1H), 7.48(s,1H), 7.79(d,1H), 8.62(s,1H), 9.06(s, 1H), 11.49(s,1H).

Example 2

3-Chloro-2-(4-cyano-3-cyclopropylcarbonylmethoxyphenyl)-5-trifluoromethylpyridine (No. Ih.09)

A mixture of 1.5 g of 3-chloro-2-(4-cyano-3-hydroxyphenyl)-5-trifluoromethylpyridine, 1.2 g of bromomethyl cyclopropyl ketone, 1.5 g of potassium carbonate and 50 ml of anhydrous dimethylformamide was stirred for 40 hours at 23° C. After addition of 200 ml of water, the mixture was extracted three times with 50 ml of methyl tert-butyl ether each time. The combined organic phases were washed with 50 ml of water, then dried over sodium sulfate and concentrated. The residue which remained was crystallized by triturating with n-hexane. Yield: 1.6 g of white crystals having a melting point of 115°–116° C.

Use examples (herbicidal activity)

It was possible to show the herbicidal action of the substituted 2-phenylpyridines I by the following greenhouse tests:

The cultivation containers used were plastic flowerpots containing loamy sand with about 3.0% humus as a substrate. The seeds of the test plants were sown separately according to species.

In the case of pre-emergence treatment, the active compounds suspended or emulsified in water were applied directly after sowing by means of finely dispersing nozzles. The containers were lightly watered to promote germination and growth, and then covered with transparent plastic hoods until the plants had taken root. This covering causes uniform germination of the test plants if this has not been adversely affected by the active compounds.

For the purpose of post-emergence treatment, the test plants were first raised, depending on growth form, up to a growth height of from 3 to 15 cm, and only then treated with the active compounds suspended or emulsified in water. For this purpose, the test plants were either sown directly and cultivated in the same containers or they were first raised separately as seedlings and transplanted into the test containers a few days before treatment. The application rate for post-emergence treatment was 0.0156 or 0.0078 kg/ha of a.s. (active substance).

The plants were kept in a species-specific manner at 10°–25° C. or 20°–35° C. The test period extended over 2 to 4 weeks. During this time, the plants were tended and their reaction to the individual treatments was evaluated.

Assessment was carried out on a scale from 0 to 100. 100 in this case means no emergence of the plants or complete destruction at least of the above-ground parts and 0 means no damage or normal course of growth.

The plants used in the greenhouse tests consist of the following species:

| Botanical name | Common name |
|---|---|
| Abutilon theophrasti | velvet leaf |
| Solanum nigrum | black nightshade |

At an application rate of 0.0156 or 0.0078 kg/ha of a.s.; the compounds No. Ia.09 and No. Ih.09 showed a very good action against the abovementioned plants post-emergence.

Use examples (desiccant/defoliant activity)

The test plants used were young, 4-leaved (without seed leaves) cotton plants, which were raised under greenhouse conditions (rel. atmospheric humidity 50 to 70%; day/night temperature 27°/20° C).

The young cotton plants were subjected to foliar treatment until dripping wet with aqueous preparations of the active compounds (with addition of 0.15% by weight of the fatty alcohol alkoxylate Plurafac LF 700, based on the spray liquor). The amount of water applied was the equivalent of 1000 l/ha. After 13 days, the number of leaves shed and the degree of defoliation was determined in %.

In the case of the untreated control plants, no leaf fall occurred.

We claim:

1. A substituted 2-phenylpyridine of the general formula I

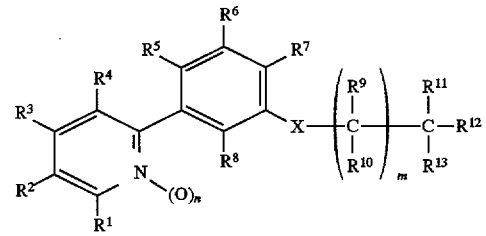

where the variables have the following meanings:

n is 0 or 1;

R$^1$, R$^3$ and R$^4$ independently of one another are hydrogen, halogen, C$_1$–C$_4$-alkyl, C$_1$–C$_4$-haloalkyl, hydroxyl, C$_1$–C$_4$-alkoxy, C$_1$–C$_4$-haloalkoxy, nitro, amino, Cl-C$_4$-alkylamino, di-(C$_1$–C$_4$-alkyl)-amino, mercapto, C$_1$–C$_4$-alkylthio, C$_1$–C$_4$-haloalkylthio, cyano, carboxyl, aminocarbonyl, (C$_1$–C$_4$-alkylamino)carbonyl or di-(C$_1$–C$_4$-alkyl)-aminocarbonyl;

R$^2$ is hydrogen, halogen, C$_1$–C$_4$-alkyl, C$_1$–C$_4$-haloalkyl, cyano, nitro, amino, hydroxyl, C$_1$–C$_4$-haloalkoxy, mercapto, C$_1$–C$_4$-alkylthio, C$_1$–C$_4$-haloalkylthio, C$_1$–C$_4$-alkylsulfinyl, C$_1$–C$_4$-haloalkylsulfinyl, C$_1$–C$_4$-alkylsulfonyl or C$_1$–C$_4$-haloalkylsulfonyl;

R$^5$ is hydrogen, halogen or cyano;

R$^6$ and R$^8$ independently of one another are hydrogen or halogen;

R$^7$ is hydrogen, cyano, nitro, hydroxyl, trifluoromethylsulfonyloxy, halogen, C$_1$–C$_4$-alkyl, C$_1$–C$_4$-haloalkyl, C$_1$–C$_4$-alkoxy or C$_1$–C$_4$-haloalkoxy;

X is oxygen or sulfur,

R$^9$ and R$^{10}$ independently of one another are hydrogen or C$_1$–C$_4$-alkyl;

m is 1, 2, 3 or 4;

$R^{11}$ is $C_1$-$C_6$-alkyl, $C_3$-$C_6$-cycloalkyl, $C_1$-$C_4$-haloalkyl having one to five halogen atoms, $C_2$-$C_4$-alkenyl, $C_2$-$C_4$-haloalkenyl having one to three halogen atoms, ($C_1$-$C_4$-alkoxy)carbonyl, ($C_1$-$C_4$-alkoxy)carbonyl-($C_1$-$C_4$-alkyl), unsubstituted or mono- to trisubstituted phenyl, unsubstituted or mono- or disubstituted thienyl, furanyl, tetrahydrofuranyl, pyrrolyl, oxazolyl, isoxazolyl, thiazolyl, isothiazolyl, pyridyl or pyrimidyl, where the substituents selected in each case are from the group consisting of nitro, cyano, halogen, $C_1$-$C_4$-alkyl and $C_1$-$C_4$-alkoxy;

$R^{12}$ and $R^{13}$ independently of one another are $C_1$-$C_4$-alkoxy or $C_1$-$C_4$-alkylthio or, together with the common carbon atom to which they are bonded, are the carbonyl group, a group

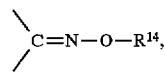

where $R^{14}$ is hydrogen, $C_1$-$C_4$-alkyl, $C_2$-$C_6$-alkenyl, $C_2$-$C_6$-haloalkenyl having one to three halogen atoms, ($C_1$-$C_4$-alkoxy)carbonyl-($C_1$-$C_4$-alkyl) or benzyl, or a heterocycle

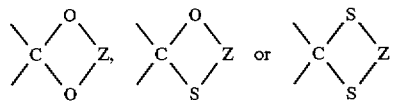

where Z is an ethylene or trimethylene chain in which, if desired, one to four hydrogen atoms can be substituted by $C_1$-$C_4$-alkyl or ($C_1$-$C_4$-alkoxy)carbonyl in each case, or the agriculturally utilizable salts of the compounds I.

2. A substituted 2-phenylpyridine of the formula I as claimed in claim 1, where n is 0, $R^1$, $R^3$ and $R^4$ independently of one another are hydrogen or halogen, $R^2$ is halogen or $C_1$-$C_4$-haloalkyl having one to five halogen atoms, $R^5$ is hydrogen or halogen, $R^6$ is hydrogen, $R^7$ is halogen or cyano, $R^8$ is hydrogen, X is oxygen, $R^9$ and $R^{10}$ independently of one another are hydrogen or $C_1$-$C_4$-alkyl, m is one, $R^{11}$ is $C_1$-$C_6$-alkyl or $C_3$-$C_6$-cycloalkyl, $R^{12}$ and $R^{13}$, together with the common carbon atom to which they are bonded, are the carbonyl group.

3. A herbicidal composition containing a herbicidally active amount of at least one substituted 2-phenylpyridine of the formula I or of an agriculturally utilizable salt of I, as claimed in claim 1, and at least one inert liquid and/or solid carrier and also, if desired, at least one surface-active substance.

4. A composition for the desiccation and/or defoliation of plants, containing an amount of at least one substituted 2-phenylpyridine of the formula I or of an agriculturally utilizable salt of I, as claimed in claim 1, which has desiccant and/or defoliant activity, and at least one inert liquid and/or solid carrier and also, if desired, at least one surface-active substance.

5. A process for preparing herbicidally active compositions, which comprises mixing a herbicidally active amount of at least one substituted 2-phenylpyridine of the formula I or of an agriculturally utilizable salt of I, as claimed in claim 1, and at least one inert liquid and/or solid carrier and also, if desired, at least one surface-active substance.

6. A process for preparing compositions having desiccant and/or defoliant activity, which comprises mixing an amount of at least one substituted 2-phenylpyridine of the formula I or of an agriculturally utilizable salt of I, as claimed in claim 1, having desiccant and/or defoliant activity, and at least one inert liquid and/or solid carrier and also, if desired, at least one surface-active substance.

7. A method of controlling undesired vegetation, which comprises allowing a herbicidally active amount of at least one substituted 2-phenylpyridine of the formula I or of an agriculturally utilizable salt of I, as claimed in claim 1, to act on plants, their habitat or on seed.

8. A method for the desiccation and/or defoliation of plants, which comprises allowing an amount of at least one substituted 2-phenylpyridine of the formula I or of an agriculturally utilizable salt of I, as claimed in claim 1, having desiccant and/or defoliant activity, to act on plants.

9. A method as claimed in claim 8, wherein cotton is treated.

10. A process for preparing substituted 2-phenylpyridines of the formula I as claimed in claim 1, which comprises reacting a 3-pyridyl(thio)phenol of the formula III

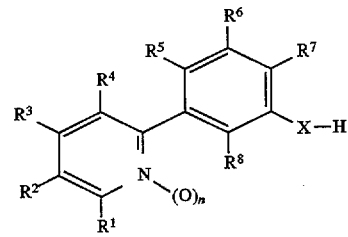

in an inert solvent or diluent, if desired in the presence of a base, with an alkylating agent of the formula IV

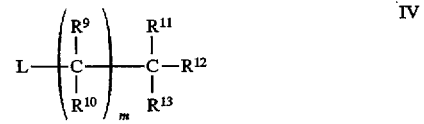

where L is chlorine, bromine, iodine, methylsulfonyloxy, trifluoromethylsulfonyloxy, phenylsulfonyloxy or p-tolylsulfonyloxy.

11. A process for preparing substituted 2-phenylpyridines of the formula I as claimed in claim 1, where n is 1 and X is oxygen, which comprises oxidizing the corresponding substituted 2-phenylpyridines, where n is zero and X is oxygen, in a manner known per se in an inert solvent or diluent.

* * * * *